United States Patent [19]

Klein et al.

[11] 3,954,889

[45] May 4, 1976

[54] PROCESS FOR THE PRODUCTION OF 1,1,3,3-SUBSTITUTED HYDROXYINDANES

[75] Inventors: Alfons Klein, Dusseldorf; Karlfried Wedemeyer, Cologne; Jürgen Thies, Leichlingen, all of Germany

[73] Assignee: Bayer Aktiengesellschaft, Leverkusen, Germany

[22] Filed: Jan. 8, 1974

[21] Appl. No.: 431,801

[30] Foreign Application Priority Data
Jan. 31, 1973 Germany............................. 2304588
Apr. 16, 1973 Germany............................. 2319079

[52] U.S. Cl...................... 260/619 R; 260/607 R; 260/609 E; 260/619 D; 260/619 F; 260/62 R; 260/620; 260/624 R; 260/626 R; 260/626 T
[51] Int. Cl.$^2$................. C07C 37/00; C07C 37/14; C07C 39/12
[58] Field of Search......... 260/621 R, 619 F, 626 R, 260/626 T, 624 R, 620, 619 R, 619 D

[56] References Cited
UNITED STATES PATENTS

| | | | |
|---|---|---|---|
| 1,972,599 | 9/1934 | Perkins et al. .................. | 260/621 D |
| 2,091,565 | 8/1937 | Perkins et al. .................. | 260/621 D |
| 2,109,015 | 2/1938 | Niederl et al. ................... | 260/621 R |
| 2,265,583 | 12/1941 | Stevens et al. ................... | 260/621 D |
| 2,948,704 | 8/1960 | Morris............................. | 260/621 R |
| 3,057,929 | 10/1962 | Arrigo............................. | 260/621 D |
| 3,644,540 | 2/1972 | Wood et al. ..................... | 260/626 R |

*Primary Examiner*—Norman Morgenstern
*Attorney, Agent, or Firm*—Burgess, Dinklage & Sprung

[57] ABSTRACT

1,1,3,3-substituted hydroxyindanes of the formula

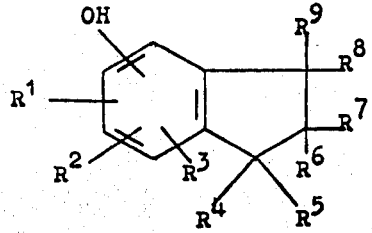

wherein
$R^1$ is selected from the group of hydrogen, halogen and optionally substituted alkyl, cycloalkyl, aralkyl and aryl and the group

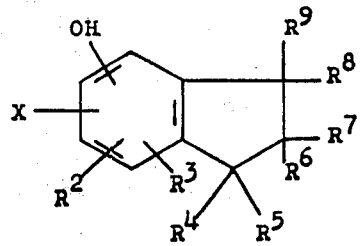

wherein
X is sulphur or the group
$R^2$ and $R^3$ can be the same or different and are selected from the group of hydrogen, halogen and optionally substituted alkyl, cycloalkyl, aralkyl and aryl group, or, if
$R^2$ and $R^3$ are in the ortho position to each other, they may form a condensed carbocyclic 5-membered ring together with the carbon atoms of the benzene ring to which they are attached as substituents,
$R^4$, $R^5$, $R^6$, $R^7$, $R^8$ and $R^9$ are the same or different and are selected from the group of optionally substituted alkyl, cycloalkyl, aralkyl and aryl or
$R^4$ and $R^5$ and/or $R^6$ and $R^7$ and/or $R^8$ and $R^9$ can form a cycloaliphatic ring together with the carbon atom to which they are attached as substituents or
$R^6$ and/or $R^7$ can also be hydrogen and
$R^{10}$ and $R^{11}$ can be identical or different and are selected from the group of hydrogen and optionally substituted alkyl or
$R^{10}$ and $R^{11}$ can form a cycloaliphatic ring together with the carbon atom to which they are attached as substituents.

The foregoing compounds are prepared by reacting an alkyl phenol in the presence of an acid catalyst at temperatures of from 100°–350°C with an olefine.

11 Claims, No Drawings

PROCESS FOR THE PRODUCTION OF 1,1,3,3-SUBSTITUTED HYDROXYINDANES

BACKGROUND

This invention relates to new 1,1,3,3-substituted hydroxyindanes and to processes for preparing them.

It is known that 4,6-diisopropyl-1,1-dimethyl-5-hydroxyindane can be prepared by reacting 2,6-isopropylphenol with isoprene in the presence of an acid catalyst (British Pat. No. 1,199,695). It is also known that 4-hydroxy-indanes can be prepared by a process of molecular rearrangement of chromans with molar quantities of aluminium chloride (U.S. Pat. No. 3,057,929).

These known processes, however, are not generally applicable and can only be used for preparing the special hydroxyindanes mentioned above.

SUMMARY

New 1,1,3,3-substituted hydroxyindanes have now been found which correspond to the following general formula

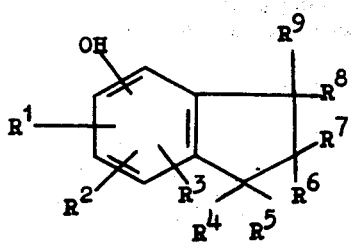

in which
  $R^1$ represents hydrogen, halogen or an optionally substituted alkyl, cycloalkyl, aralkyl or aryl group or the group

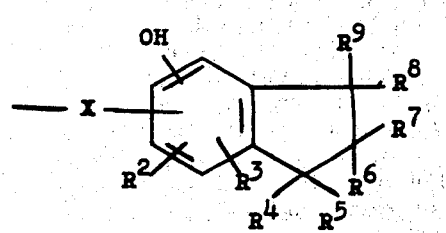

in which
  X represents sulphur or the group

$R^2$ and $R^3$ which may be identical or different represent hydrogen, halogen or an optionally substituted alkyl, cyaloalkyl, aralkyl or aryl group or if $R^2$ and $R^3$ are in the ortho-position to each other they form a condensed 5-membered carbocyclic ring with the C atoms substituted by them in the benzene ring;

$R^4$, $R^5$, $R^6$, $R^7$, $R^8$ and $R^9$ may be identical or different and represent an optionally substituted alkyl, cycloalkyl, aralkyl or aryl group; or $R^4$ and $R^5$ and/or $R^6$ and $R^7$ and/or $R^8$ and $R^9$ may form a cycloaliphatic ring, in each case together with the carbon atom which carries them as substituents; or $R^6$ and/or $R^7$ may also represent hydrogen; and $R^{10}$ and $R^{11}$ may be identical or different and represent hydrogen or an optionally substituted alkyl group or $R^{10}$ and $R^{11}$ may form a cycloaliphatic ring together with the C atom which carries them as substituents.

DESCRIPTION

The halogens ($R^1$,$R^2$,$R^3$) may be fluorine, chlorine, bromine or iodine but chlorine and bromine are preferred.

The optionally substituted alkyl groups may be straight chain or branched chain alkyl groups with up to 12 and preferably up to 8 carbon atoms and in particular up to 4 carbon atoms, for example methyl, ethyl, propyl, isopropyl, butyl, isobutyl, t.-butyl, amyl, isoamyl or the isomeric hexyl, heptyl or octyl groups.

The following are preferred: Methyl, ethyl, propyl, isopropyl, butyl, isobutyl, t.-butyl, amyl, isoamyl and hexyl groups.

The optionally substituted cycloalkyl groups may be groups with from 3 to 8 carbon atoms, preferably the cyclopentyl or cyclohexyl group.

The optionally substituted aralkyl groups may be groups with up to 6 carbon atoms in the aliphatic part and up to 14 carbon atoms in the aromatic part. The following are examples of the aliphatic part of the group: Methyl, propyl, isopropyl, butyl, isobutyl, pentyl and hexyl. The aromatic part of the group may be phenyl, naphthyl or anthranyl. The preferred araliphatic groups are benzyl and ethylphenyl.

The optionally substituted aryl groups may be, for example, the following: Phenyl, naphthyl or anthranyl; but phenyl is preferred.

Substituents on the optionally substituted groups $R^1$ to $R^9$ may be, for example, alkyl groups with up to 12 carbon atoms, preferably up to 6 carbon atoms. They may be straight chain or branched, for example methyl, ethyl, propyl, isopropyl, butyl or t.-butyl.

It has also been found that these new 1,1,3,3-substituted hydroxyindanes can easily be prepared by reacting an alkylphenol of the general formula

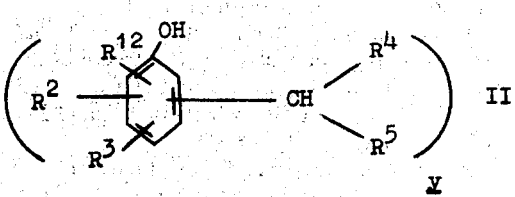

in which
  $R^{12}$ represents hydrogen, halogen or an optionally substituted alkyl, cycloalkyl, aralkyl or aryl group;

and $R^2$, $R^3$, $R^4$ and $R^5$ have the meanings indicated above and y represents the integer 1 or 2 in the presence of an acid catalyst at a temperature of from 100° to 350°C with an olefine in which at least one carbon atom with a double bond is attached exclusively to a carbon atom that is to say the olefine contains the group

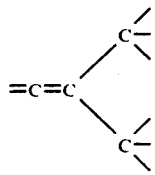

or by reacting the compound of general formula II under these conditions with a compound which yields the corresponding olefin in situ.

The temperatures employed are preferably within the range of 110° to 250°C, in particular from 120° to 180°C.

The acid catalyst used in the process according to the invention may generally be the same known acid catalysts as those used in known manner for alkylating phenols (see DAS No. 1 518 460, DOS No. 1 643 390, DOS No. 2 034 369 and DOS No. 2 111 193).

The following are mentioned as examples of such catalysts:

Lewis acids such as $AlCl_3$ and $BF_3$. Protonic acids, that is to say acids which give up a proton when they dissociate, in particular mineral acids such as sulphuric acid, phosphoric acid, hydrochloric acid and perchloric acid. Silicas and Fuller's earths such as Montmorrillonite, silicoaluminates and silica gel. The silicas suitable for this purpose are finely divided materials which contain silicic acid and/or aluminum oxide. Silicas and Fuller's earths of this kind may either be used without a preliminary treatment or they may first be activated with mineral acids such as sulphuric acid, phosphoric acid, hydrochloric acid, perchloric acid or hydrofluoric acid. Natural or synthetic ion exchangers such as zeolites or exchanger resins. These exchanger resins are insoluble resins which consist of inert two-dimensionally or three-dimensionally cross-linked polymers which are substituted with reactive groups such as phosphoric, phosphonic, sulphuric or sulphonic acid groups.

The catalysts used in the process according to the invention are preferably mineral acids, Fuller's earths, silicas and exchanger resins.

The preferred mineral acids are sulphuric acid, hydrochloric acid and phosphoric acid.

The silicas and Fuller's earths are preferably those which have been activated by acid treatment in known manner (Chemie fur Labor and Betrieb, 1956, page 422; Ullmann, 3rd Edition Volume 9, page 271 et seq; Volume 8, pages 801 to 804).

The following are specific examples of suitable ion exchanger resins: Styrene-divinylbenzene resins, cross-linked styrene resins, phenol formaldehyde resins and benzene formaldehyde resins. All of these are preferably substituted with sulphonic acid groups. Resins which contain one sulphonic acid group for every 0.5 to 2 monomer units of the resin are particularly suitable (Ullmann, 3rd Edition, Volume 8, pages 806 to 822, in particular page 816; German Pat. No. 915 267).

The reaction may also be carried out with mixtures of the above mentioned catalysts.

The quantity of catalyst used in the process according to the invention may vary within a wide range. In general about 2 to 30 % by weight, preferably 7 to 14 % by weight, based on the quantity of alkylphenol of Formula II are used.

The alkylphenols of the general formula II which are used as starting materials in the process according to the invention and in which y = 1 are known per se. The following are examples: o-, m- and p-isopropyl-phenol; o-, m- and p-cyclopentyl-phenol; o-, m- and p-cyclohexyl-phenol; o-, m- and p-isobutyl-phenol; 1-phenyl-1-(4-hydroxy-phenyl)-ethane; 3-methyl-6-isopropyl-phenol; 3-methyl-5-isopropyl-phenol; 2-ethyl-4-cyclohexyl-phenol; 2-methyl-4-isobutyl-phenol; 2-chloro-4-isopropyl-phenol.

The alkylphenols of the general formula II in which y =0 2 are also already known. The following are specific examples: 3,5-Diisopropylphenol, 3,5-dicyclopentyl-phenol, 3,5-di-sec.-butyl-phenol, 3,5-dicyclohexyl-phenol, 3-isopropyl-5-cyclopentyl-phenol, 3-cyclopentyl-5-sec.-butyl-phenol, 2,6-diisopropylphenol, 2,6-dicyclopentyl-phenol, 2-isopropyl-6-cyclopentylphenol and 3,4-diisopropylphenol.

Olefines which contain the group

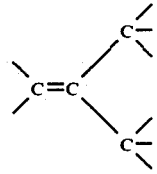

that is to say in which at least one carbon atom which carries a double bond is linked only to other carbon atoms, in other words so-called tertiary olefines, are also already known. The following are specific examples: 2-Methyl-propene, 2-methyl-butene-(1), 2-methyl-butene-(2), 2,3-dimethyl-butene-(1), 2,3-dimethyl-butene-(2), 2-methyl-2-phenyl-propene-(1). 2-methyl-propene (isobutylene) is preferred.

The molar ratio of alkylphenol of the general formula II to tertiary olefine may vary within wide limits. The phenol and olefine may be used in approximately equimolar proportions but it is preferred to use about 2 mols of olefine to 1 mol of phenol. Even more than 2 mols of olefine per mol of phenol may be used, in which case the phenol nucleus may also be substituted by one or more alkyl groups which correspond to the tertiary olefine used.

The process according to the invention may be carried out at normal pressure or at elevated pressures of up to 60 atmospheres, preferably up to 20 atmospheres.

The reaction is preferably carried out within a pressure range of from 1 to 10 atmospheres.

The process according to the invention may also be carried out in an inert solvent or diluent, for example in aliphatic and aromatic hydrocarbons, in particular hexane and heptane, benzene, toluene and xylene.

The process according to the invention is generally carried out by introducing the alkylphenol of the general formula II, optionally in the form of a solution in an inert solvent, into a suitable reaction vessel, e.g. an autoclave, adding the selected catalyst, heating to the chosen reaction temperature, adding the olefine with stirring and then leaving the mixture to react for about 0.5 to 5 hours with stirring.

After termination of the reaction, the reaction product is worked up in conventional manner by removing the catalyst from the reaction vessel in known manner, e.g. by filtration, centrifuging or washing, depending on the nature of the catalyst, and then isolating the reaction products from the reaction mixture which is now free from catalyst, this being also carried out by known methods such as distillation or crystallisation.

The process according to the invention can be carried out continuously in a homogeneous phase with fixed bed or fluidised bed catalysts. Various apparatus and methods of procedure suitable for carrying out the process of the invention are known in the art. The process according to the invention may be illustrated by the following reaction scheme which represents by way of example the reaction of -p-isopropyl-phenol with isobutylene:

The following are examples of phenols which are substituted with tertiary alkyl groups: o-, m- and p-tert.-butylphenol; 2,4-di-tert.-butylphenol; and 3,5-di-tert.-butylphenol.

According to a preferred embodiment of the process of the invention, alkylphenols of the general formula II which are substituted by one or more tertiary alkyl groups, i.e. in which one or more of the groups $R^{12}$, $R^2$ and $R^3$ represent tertiary alkyl groups, may be used to serve both as alkylphenols of the general formula II and at the same time as corresponding tertiary olefine. The reaction according to the invention in that case proceeds as an intramolecular reaction.

The alkylphenols of formula II which may be used for the process according to the invention may also be prepared by a one pot process from an optionally substituted phenol in a first reaction stage and then immediately converted in a second reaction stage into the hydroxyindanes by the process according to the invention. This process may, for example, be carried out as follows: The optionally substituted phenol, optionally dissolved in an inert solvent, is introduced into the reaction vessel and then the catalyst is added. The olefine is then added with stirring in the course of about 0.5 to 5 hours, depending on the size of the batch, at a

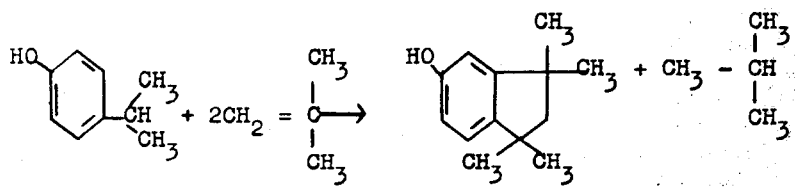

Particularly good yields can be obtained by using 2 mols of tertiary olefine per mol of phenol as starting material. This proportion of starting materials is therefore generally preferred.

Instead of using a tertiary olefine, the process may also be carried out by using compounds which yield the corresponding olefine in situ in the course of the reaction, for example the corresponding alcohols or tertiary alkyl phenols.

Isobutanol, tertiary butanol and 2-methyl-butanol-(2) are examples of alcohols which may be used as starting materials by this method instead of the corresponding olefines.

Furthermore, the alkylphenols of the general formula II may also be reacted with phenols which are substituted with one or more tertiary alkyl groups instead of with the corresponding tertiary olefine. The tertiary olefine is then obtained in situ from the tertiary alkyl group. Thus, for example, the reaction of 4-isopropyl-phenol and 4-tert.-butyl phenol by the process according to the invention yields not only the reaction product according to the invention, which is 1,1,3,3-tetramethyl-5-hydroxyindane, but also phenol. This proves that 4-tertiary butyl-phenol yields isobutylene in situ in accordance with the following reaction scheme:

temperature of from 40° to 100°C and at normal or elevated pressure, preferably at a pressure of up to about 60 atmospheres and in particular up to about 10 atmospheres, and when alkylation has been completed, the temperature is raised to the reaction temperature selected for the process according to the invention. The same or some other olefine is then added in the second stage of the process by the general procedure described above and the process according to the invention is carried out.

If alkylphenols of the general formula II in which y = 2 are used as starting materials for the hydroxyindanes according to the invention, then the hydroxyindanes of formula I correspond in particular to the following general formulae

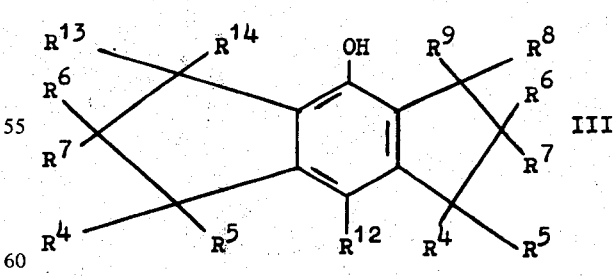

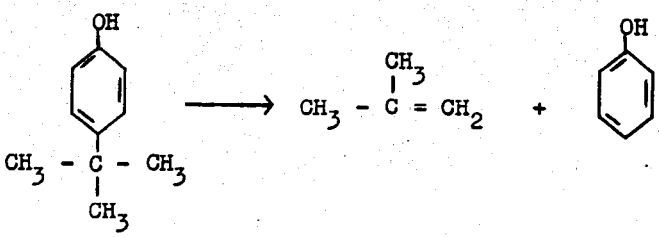

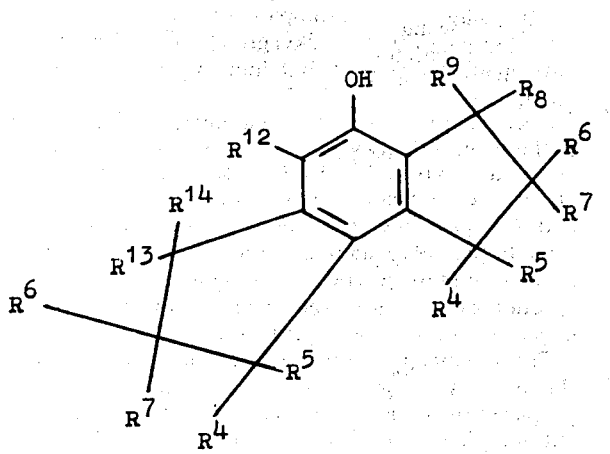

IV in which
R⁴, R⁵, R⁶, R⁷, R⁸, R⁹ and R¹² have the meanings already indicated above: and
-R¹³ and R¹⁴ which may be identical or different represent an optionally substituted alkyl, cycloalkyl, aralkyl or aryl group or form a cycloaliphatic ring together with the carbon atom which carries them as substituents.

The symbols $R^{12}$, $R^{13}$ and $R^{14}$ cover the same meanings as the groups $R^1$ to $R^{11}$ also as regards the substituents. A special group of the new 1,1,3,3-substituted hydroxyindanes correspond substantially to the following formula

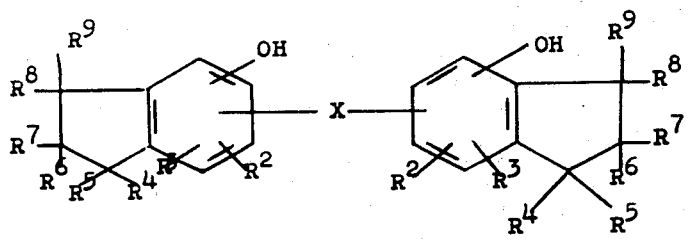

(V)

in which
$R^2$, $R^3$, $R^4$, $R^5$, $R^6$, $R^7$, $R^8$, $R^9$ and X are as just defined.

The compounds of the general formula V may be prepared in known manner by reacting compounds of the general formula

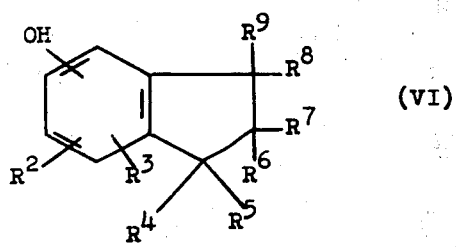

(VI)

in which
$R^2$, $R^3$, $R^4$, $R^5$, $R^6$, $R^7$, $R^8$ and $R^9$ are as just defined with sulphur dichloride or aldehydes or ketones of the general formula

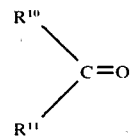

(VII)

in which
$R^{10}$ and $R^{11}$ have the meanings indicated above.

The following are examples of aldehydes and ketones which may be used as starting compounds for preparing the compounds according to the invention which are represented by the general formula V: Formaldehyde, acetaldehyde, propionaldehyde, butyraldehyde, isobutyraldehyde, hexanal, heptanal, 2-ethylhexanal, acetone, methyl ethyl ketone, diethylketone, methylisopropylketone, diisopropylketone, methylisobutylketone, methyl-tert.-butylketone, diisobutylketone, cyclopentanone, and cyclohexanone.

The following are examples of starting compounds of the general formula VI which may be used for preparing the compounds of the general formula V and which are in turn 1,1,3,3-substituted hydroxyindanes according to the invention and may be prepared by the process according to the invention:

5-Hydroxy-1,1,3,3-tertramethyl-indane;
5-hydroxy-6-tert.-butyl-1,1,3,3-tetramethyl-indane;
5-hydroxy-1,1,3,3,7-pentamethyl-indane;
5-hydroxy-6-cyclopentyl-1,1,3,3-tetramethyl-indane;
4-hydroxy-1,1,3,3,6-pentamethyl-indane;
5-hydroxy-1,3,3-trimethyl-1-ethyl-indane;
4-hydroxy-1,1,3-trimethyl-3-phenyl-indane;
5-hydroxy-1,3,3-trimethyl-1-phenyl-indane;
5-hydroxy-1,1-pentamethylene-3,3-dimethyl-indane;
5-hydroxy-6-tert.-butyl-1,1-pentamethylene-3,3-dimethyl-indane;
5-hydroxy-6-chloro-1,1,3,3-tetramethyl-indane;
5-hydroxy-1,1,2,3,3-pentamethyl-indane;
5-hydroxy-6-chloro-1,1-pentamethylene-3,3-dimethyl-indane;
5-hydroxy-6-chloro-1,3,3-trimethyl-1-phenyl-indane;
4-hydroxy-5-tert.-butyl-1,1,3-trimethyl-3-phenyl-indane;
5-hydroxy-6-tert.-butyl-1,1,2,3,3-pentamethyl-indane;
5-hydroxy-6-cyclopentyl-1,1,2,3,3-pentamethyl-indane;
4-hydroxy-1,1,3,3,6,7-hexamethyl-indane; and
5-hydroxy-1,1,3,3,4,7-hexamethyl-indane.

The new compounds of formula V may be prepared by methods known for preparing bis-phenols (see Ullman Enzyklopadie der technischen Chemie, 3rd Edition, Volume 13, Munich, Berlin 1962, page 448). The hydroxyindane of formula VI used as starting material is usually dissolved in an inert solvent or emulsified with the aid of an emulsifier. The selected acid catalyst, e.g. hydrochloric acid, sulphuric acid, phosphoric acid or p-toluenesulphonic acid, and the corresponding aldehyde or ketone of the general formula VII are then added and the reaction mixture is stirred for some time at an elevated temperature in the region of from 40°C to 150°C, preferably from 80° to 120°C.

The acid catalysts described above may generally also be used. It is generally unnecessary to use an acid catalyst if the reaction is carried out with sulphur chloride instead of a compound of the general formula VII since sulphur dichloride itself as well as the hydrogen chloride evolved act as catalysts.

After termination of the reaction, the reaction product which precipitates on cooling in the form of a solid is isolated in known manner, e.g. by filtration or by centrifuging. Depending on the nature of the catalyst used, it can be removed in known manner by washing, if indicted after first converting it into a soluble salt by neutralizing it, or the catalyst optionally together with solvent may be removed by distillation, e.g. in the case of hydrochloric acid.

As already mentioned above, the reaction may either be carried out solvent-free or in a homogeneous phase using organic solvents such as glacial acetic acid and chlorinated hydrocarbons or in an aqueous emulsion. If sulphur dichloride is used as starting material instead of compounds of the general formula VII, the process may also be carried out as already described (see loc. cit. page 452).

The following are examples of the new 1,1,3,3-substituted hydroxyindanes of the formula V which can be obtained as described above:

Bis-[5-hydroxy-1,1,3,3-tetramethyl-indanyl-(6)]-methane;
2-methyl-1,1-bis-[5-hydroxy-1,1,3,3-tetramethyl-indanyl-(6)]-propane;
bis-[5-hydroxy-1,1,3,3-tetramethyl-indanyl-(6)]-sulphide;
2,2-bis-[5-hydroxy-1,1,3,3-tetramethyl-indanyl-(6)]-propane;
2,2-bis-[5-hydroxy-6-tert.-butyl-1,1,3,3-tetramethyl-indanyl-(4)]-propane;
bis-[5-hydroxy-6-tert.-butyl-1,1,3,3-tetramethyl-indanyl-(4)]-methane;
2-methyl-1,1-bis-[5-hydroxy-6-tert.-butyl-1,1,3,3-tetramethyl-indanyl-(4)]-propane;
1,1-bis-[5-hydroxy-6-tert.-butyl-1,1,3,3-tetramethyl-indanyl-(4)]-butane;
bis-[5-hydroxy-6-cyclopentyl-1,1,3,3-tetramethyl-indanyl-(4)]-methane;
2-methyl-1,1-bis-[5-hydroxy-6-cyclopentyl-1,1,3,3-tetramethyl-indanyl-(4)]-propane;
bis-[5-hydroxy-6-chloro-1,1,3,3-tetramethyl-indanyl-(4)]-methane;
1,1-bis-[5-hydroxy-6-chloro-1,1,3,3-tetramethyl-indanyl-(4)]-butane;
2-methyl-1,1-bis-[5-hydroxy-6-chloro-1,1,3,3-tetramethyl-indanyl-(4)]-propane;
bis-[5-hydroxy-1,3,3-trimethyl-1-phenyl-indanyl-(6)]-methane;
2,2-bis-[5-hydroxy-1,3,3-trimethyl-1-phenyl-indanyl-(6)]-propane;
bis-[5-hydroxy-1,1-pentamethylene-3,3-dimethyl-indanyl-(6)]-methane;
2-methyl-1,1-bis[5-hydroxy-1,1-pentamethylene-3,3-dimethyl-indanyl-(6)]-propane;
bis-[5-hydroxy-1,1-pentamethylene-3,3-dimethyl-6-tert.-butyl-indanyl-(4)]-methane;
bis-[5-hydroxy-1,1,3,3-tetramethyl-6-tert.-butyl-indanyl-(4)]-sulphide;
bis-[5-hydroxy-1,1,3,3-tetramethyl-6-cyclopentyl-indanyl-(4)]-sulphide;
bis-[5-hydroxy-1,1,3,3-tetramethyl-6-chloro-indanyl-(4)]-sulphide;
bis-[5-hydroxy-1,1-pentamethylene-3,3-dimethyl-indanyl-(6)]-sulphide;
bis-[5-hydroxy-1,1-pentamethylene-3,3-dimethyl-6-tert.-butyl-indanyl-(4)]-sulphide;
bis-[5-hydroxy-1,3,3-trimethyl-1-phenyl-indanyl-(6)]-sulphide;
2,2-bis-[4-hydroxy-1,1,3-trimethyl-3-phenyl-indanyl-(7)]-propane;
1,1-bis-[5-hydroxy-1,1,3,3-tetramethyl-indanyl-(6)]-cyclohexane;
1,1-bis-[5-hydroxy-1,1,3,3-tetramethyl-6-tert.-butyl-indanyl-(4)]-cyclohexane;
1,1-bis-[5-hydroxy-1,1,3,3-tetramethyl-indanyl-(6)]-cyclopentane;
1,1-bis-[5-hydroxy-1,1,3,3-tetramethyl-6-tert.-butyl-indanyl-(4)]-cyclopentane;

1,1-bis-[5-hydroxy-1,1,3,3-tetramethyl-6-chloro-indanyl-(4)]-cyclohexane.

The new hydroxyindanes are valuable intermediate products, praticularly for the synthesis of insecticides, germicides or fungicides and they may also be used as aromatic substances and antioxidants (British Pat. No. 1,199,695 and U.S. Pat. No. 2,057,929).

By virtue of their reducing action, the new hydroxyindanes may be used in known manner as developers in photographic materials and processes.

The new hydroxyindanes may be used in particular as reducing agents for photographic materials used for dry methods of producing photographic copies on a layer which consists mainly of light insensitive, reducible silver salts, reducing agents and a toner and optionally also a light-sensitive heavy metal compound and/or a polymethine sensitizer for spectrally sensitizing the light insensitive silver compound.

Materials and processes of this kind have been described in, for example, German Pat. Nos. 1,300,014, and 1,234,243, in U.S. Pat. Nos. 3.457,075 and 3,619,237, in French Pat. No. 2,037,847 and in Belgian Pat. Nos. 770,971, 771,274 and 771,730.

The acid activated Fuller's earth used in the following examples was obtained from Sudchemie AG, Munich under the trade name "K 10 SF" and the ionic exchanger was prepared in accordance with German Pat. No. 915,267.

The abbreviations Mp. and Bp. denote melting point and boiling point and the suffix after the abbreviation Bp. indicates the pressure in Torr.

EXAMPLE 1

112 g (2 mol) of isobutylene were pumped for 1 hour into 136 g (1 mol) of 4-isopropyl-phenol in 100 ml of toluene and 30 g of an acid activated Fuller's earth in an autoclave with stirring at 150°C. The reaction mixture was then stirred for 6 hours at 150°C. After removal of the catalyst by filtration, 120 g of pure 1,1,3,3-tetramethyl-5-hydroxyindane were obtained by fractional distillation; Bp$_{12}$: 144°C; Mp: 119°C.

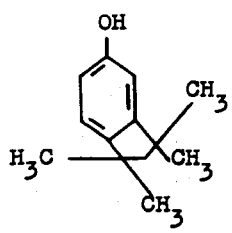

EXAMPLE 2

112 g (2 mol) of gaseous isobutylene were introduced into 136 g (1 mol) of 3-isopropyl-phenol and 10 g of an acid activated Fuller's earth in a glass flask at 150°C with stirring. Stirring was then continued for 1 hour at 150°C. After removal of the catalyst by suction filtration the product was worked up by fractional distillation. At bp$_{12}$: 144°C there were obtained 71 g of 1,1,3,3-tetramethyl-5-hydroxy-indane and at bp$_{12}$: 149°–155°C 63 g of a fraction from which 33 g of 1,1,3,3-tetramethyl-5-hydroxy-6-tert.-butyl-indane were obtained by recrystallisation from cyclohexane; m.p. 114°C.

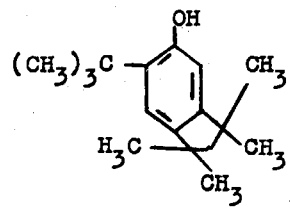

EXAMPLE 3

160 g (2.85 mol) of isobutylene were introduced into 210 g (1.4 mol) of 3-methyl-5-isopropyl-phenol and 21 g of an acid activated Fuller's earth as described in Example 2. Distillation yields at bp$_{12}$: 142°–144°C 52 g of a fraction from which 24 g of 1,1,3,3,6-pentamethyl-4-hydroxy-indane were obtained by recrystallisation from petroleum ether; mp: 66°C.

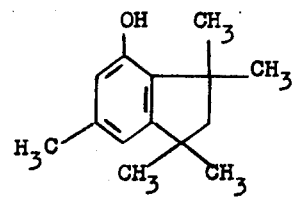

121 g of another fraction which boils at bp$_{12}$: 160°–170°C yields 77 g of 1,1,3,3,7-pentamethyl-5-hydroxy-indane, mp: 120°C, by recrystallisation from petroleum ether.

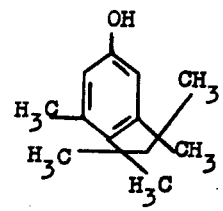

EXAMPLE 4

150 g (1 mol) of 4-sec.-butyl-phenol and 10 g of an acid activated Fuller's earth were reacted with 112 g (2 mol) of isobutylene as described in Example 2. The resulting crude mixture was fractionated in a 1 m column filled with glass bodies. At bp$_{12}$: 155°–160°C there are obtained 68 g of a fraction from which 48 g of 1,3,3-trimethyl-1-ethyl-5-hydroxy-indane were obtained by recrystallisation from petroleum ether; mp: 86°C.

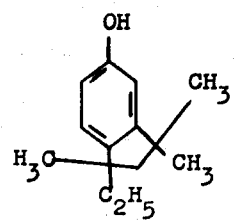

EXAMPLE 5

68 g (0.5 mol) of 3-isopropyl-phenol, 15 g of an acid activated Fuller's earth and 118 g (1 mol) of α-methylstyrene were stirred at 150°C for 5 hours. After removal of the catalyst by suction filtration and of the isopropylbenzene formed in the reaction by distillation, the residue was fractionated over a 60 cm laboratory column with filling bodies. A viscous oil containing 90 % of 1,1,3-trimethyl-3-phenyl-4-hydroxy-indane was obtained at $bp_{0.3}$: 133°–137°C.

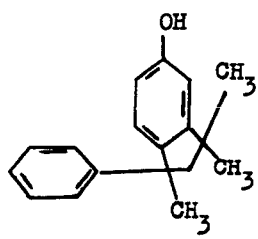

Another fraction which boiled at $bp_{0.3}$: 143°–144°C yielded 18 g of a solid compound from which 12 g of 1,3,3-trimethyl-1-phenyl-5-hydroxy-indane could be isolated by recrystallisation from ligroin; mp. 98°–100°C.

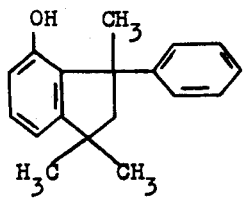

EXAMPLE 6

176 g (1 mol) of 4-cyclohexyl-phenol, 12 g of an acid activated Fuller's earth and 112 g (2 mol) of isobutylene were reacted together and worked up as described in Example 5. At $bp_{1.2}$: 144°–146°C there were obtained 49 g of a fraction from which 25 g of 1,1-pentamethylene-3,3-dimethyl-5-hydroxyindane, bp: 104°C, could be isolated by recrystallisation from petroleum ether.

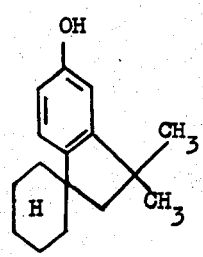

51.3 g of a fraction which boiled at $bp_{1.2}$: 154°–160°C yield 21 g of 1,1-pentamethylene-3,3-dimethyl-6-tert.-butyl-5-hydroxyindane, mp 151°C, after recrystallisation from petroleum ether.

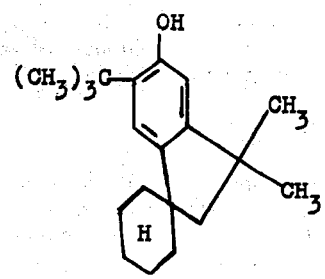

EXAMPLE 7

114 g (0.66 mol) of 2-chloro-4-isopropyl-phenol, 20 g of an acid activated Fuller's earth and 75 g (1.33 mol) of isobutylene were reacted together and worked up as described in Example 2. 41 g of 1,1,3,3-tetramethyl-6-chloro-5-hydroxy-indane were obtained; $bp_{0.2}$: 79°C; mp 52°C.

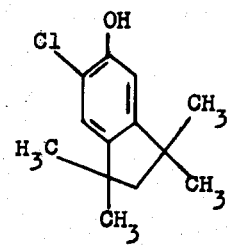

EXAMPLE 8

68 g (0.5 mol) of 3-isopropyl-phenol, 10 g of an acid activated Fuller's earth and 70 g (1 mol) of 2-methyl-butene-(2) were reacted and worked up as described in Example 5. A fraction which boiled at $bp_{12}$: 159–170°C yielded 9.5 g of 1,1,2,3,3-pentamethyl-5-hydroxy-indane, mp: 149°C, on recrystallisation from benzene.

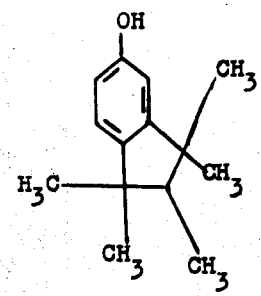

EXAMPLE 9

150 g (1 mol) of 2-isopropyl-5-methylphenol and 30 g of an acid activated Fuller's earth were introduced into an autoclave. 112 g (2 mol) of isobutylene were pumped in at 250°C with stirring and the mixture was then stirred for a further 3 hours at 250°C. After removal of the catalyst by suction filtration, 23 g of 1,1,3,3,6-pentamethyl-4-hydroxy-indane were obtained by fractional distillation.

EXAMPLE 10

136 g (1 mol) of 4-isopropyl-phenol and 30 g of an acid activated Fuller's earth were introduced into an autoclave. 112 g (2 mol) of isobutylene were pumped in at 70°C with stirring and the mixture was then stirred for 3 hours at this temperature. The temperature was then raised to 150°C and stirring was continued for 4 hours. The catalyst was removed by suction filtration and the filtrate subjected to fractional distillation. 96 g of 1,1,3,3-tetramethyl-5-hydroxy-indane were obtained.

EXAMPLE 11

75 g of 2,6-di-tert.-butyl-4-isopropyl-phenol and 10 g of an acid activated Fuller's earth were stirred in a glass flask at 150°C for 4 hours. 10.5 g of isobutylene were trapped in a deep cooling condenser. 30.5 g of 1,1,3,3-tetramethyl-5-hydroxy-indane could be obtained from the reaction mixture by distillation after removal of the catalyst.

EXAMPLE 12

100 g of 2-tert.-butyl-4-isopropyl-phenol and 10 g of an acid activated Fuller's earth were stirred in a glass flask for 4 hours at 150°C. The isobutane formed in the reaction was trapped in a deep cooling condenser. After removal of the catalyst, 28 g of 1,1,3,3-tetramethyl-5-hydroxy-indane could be obtained by fractional distillation from the reaction mixture in addition to 26 g of 4-isopropyl-phenol.

EXAMPLE 13

136 g (1 mol) of 4-isopropyl-phenol and 3 g of concentrated $H_2SO_4$ were reacted with 112 g (2 mol) of isobutylene at 150°C as described in Example 2. The catalyst was removed by washing with water. 18 g of 1,1,3,3-tetramethyl-5-hydroxy-indane were isolated by fractional distillation.

EXAMPLE 14

136 g (1 mol) of 4-isopropyl-phenol and 20 g of an aluminium silicate were reacted with 112 g (2 mol) of isobutylene in a stirrer autoclave at 180°C. 51 g of 1,1,3,3-tetramethyl-5-hydroxy-indane were obtained by fractional distillation after removal of the catalyst by suction filtration.

EXAMPLE 15

112 g (2 mol) of gaseous isobutylene were introduced into 136 g (1 mol) of 4-isopropyl-phenol and 10 ml of borofluoride etherate at 80°C with stirring. The reaction mixture was then stirred for 1 more hour at 80°C and for 5 hours at 150°C. The catalyst was removed by washing with water. 49 g of 1,1,3,3-tetramethyl-5-hydroxy-indane could be obtained from the reaction mixture by fractional distillation.

EXAMPLE 16

112 g (2 mol) of gaseous isobutylene were introduced with stirring into 136 g (1 mol) of 4-isopropyl-phenol and 30 g of an ion exchanger resin at 80°C. The reaction mixture was then stirred for one hour at 80°C and 5 hours at 150°C. The catalyst was removed by suction filtration. 21 g of 1,1,3,3-tetramethyl-5-hydroxy-indane could be obtained from the reaction mixture by fractional distillation.

EXAMPLE 17

100 g of isobutylene were pumped into 93 g of 3,5-diisopropyl-phenol and 13 g of an acid activated Fuller's earth in a stirrer autoclave at 150°C. Stirring was then continued for 4 hours at 250°C. After removal of the catalyst, the substance which crystallised from the cold reaction mixture was removed by suction filtration and recrystallised from ligroin. 54 g of 2,3;4,5-bis-[1,1,3,3-tetramethyl-trimethylene]-phenol were obtained in this way. Melting point 249°–251°C.

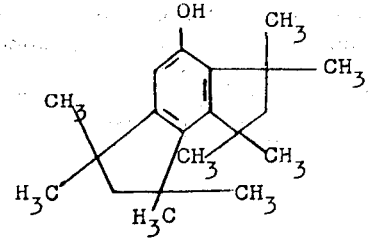

EXAMPLE 18

112 g of isobutylene were introduced with stirring into 198 g of 1-phenyl-1-(4-hydroxy-phenyl)-ethane and 30 g of an acid activated Fuller's earth at 150°C and the reaction mixture was then stirred at this temperature for 5 hours. 34 g of 1,3,3-trimethyl-1-phenyl-5-hydroxy-indane could be obtained by distillation followed by recrystallisation.

EXAMPLE 19

150 g of tert.-butanol were introduced dropwise into 136 g (1 mol) of 4-isopropyl-benzene, 200 ml of benzene and 30 g of an acid activated Fuller's earth with stirring and removal of water by azeotropic distillation. 36 g of water were separated. The isobutane formed in the reaction was collected in a deep cooling condenser attached to the apparatus. After removal of the catalyst by suction filtration, 85 g of 1,1,3,3-tetramethyl-5-hydroxy-indane were obtained by fractional distillation.

EXAMPLE 20

68 g (½ mol) of 4-isopropyl-phenol, 150 g (1 mol) of 4-tert.-butyl-phenol and 30 g of an acid activated Fuller's earth were stirred for 5 hours at 150°C. The substance which collected in the deep cooling condenser was isobutane. After removal of the catalyst by suction filtration, fractional distillation yielded 46 g of 1,1,3,3-tetramethyl-5-hydroxy-indane in addition to phenol.

EXAMPLE 21

38 g of 1,1,3,3-tetramethyl-5-hydroxyindane in 150 ml of benzene and 6.4 ml of sulphur dichloride were stirred for 3 hours at 50°C. The crystals obtained on cooling were suction filtered, dried and recrystallised from chloroform. 21 g (51 % of the theory) of bis-[5-hydroxy-1,1,3,3-tetramethyl-indanyl-(6)]-sulphide were obtained; Melting point 228°–230°C.

EXAMPLE 22

38 g of 1,1,3,3-tetramethyl-5-hydroxyindane, 300 ml of water, 6 ml of a 10 % Mersolat solution, 8 ml of concentrated hydrochloric acid and 30 ml of a 30 % by weight aqueous formaldehyde solution were stirred for 6 hours at 90° to 95°C. The crystals which precipitated on cooling were suction filtered, dried and recrystallised from methanol. 16.6 g (43 % of the theory) of bis-[5-hydroxy-1,1,3,3-tetramethyl-indanyl-(6)]-methane, melting point 207.5°C, were obtained.

EXAMPLE 23

22 g of isobutyraldehyde were slowly added to 114 g of 1,1,3,3-tetramethyl-5-hydroxy-indane and 3 g of concentrated H₂SO₄ at 120°C. The temperature was lowered to 80°C while the isobutyraldehyde was run in. The reaction mixture was then heated to 90°C for 2 hours. It was then boiled up with 400 ml of benzene, 300 ml of water and 15 g of sodium acetate. Crystals precipitated from the separated benzene layer on cooling. These were suction filtered, dried and recrystallised from dioxane. 91.2 g (70 % of the theoretical yield) of 2-methyl-1,1-bis-[5-hydroxy-1,1,3,3-tetramethyl-indanyl-(6)]-propane, melting point 220° to 221°C, were obtained.

EXAMPLE 24

A mixture of 38 g of 1,1,3,3-tetramethyl-5-hydroxy-indane, 300 ml of water, 7 ml of 10 % by weight aqueous Mersolat solution and 15 ml of concentrated hydrochloric acid and 20 g of isobutyraldehyde were stirred for 6 hours at 90° to 95°C. The crystals which precipitated on cooling were suction filtered, dried and recrystallised from dioxane. 40 g (92 % of the theoretical yield) of 2-methyl-1,1-bis-[5-hydroxy-1,1,3,3-tetramethyl-indanyl-(6)]-propane, melting point 220°–221°C, were obtained.

What is claimed is:

1. Process for preparing 1,1,3,3-substituted hydroxyindanes having the formula I

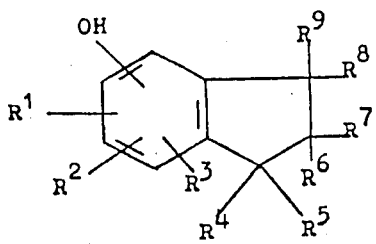

wherein
R¹, R² and R³ can be the same or different and are selected from the group of hydrogen, alkyl with up to 12 carbon atoms, cycloalkyl with 3 to 8 carbon atoms, aralkyl with up to 6 carbon atoms in the alkyl part and up to 14 carbon atoms in the aryl part, phenyl, naphthyl, anthranyl, and the foregoing substituted by alkyl with up to 12 carbon atoms;
R⁴, R⁵, R⁶, R⁷, R⁸ and R⁹ can be the same or different and are selected from the group of alkyl with up to 12 carbon atoms, cycloalkyl with 3 to 8 carbon atoms, aralkyl with up to 6 carbon atoms in the alkyl part and up to 14 carbon atoms in the aryl part, phenyl, naphthyl, anthranyl, and the foregoing substituted by alkyl with up to 12 carbon atoms; and
R⁶ and/or R⁷ can also be hydrogen;
which comprises reacting an alkylphenol having the formula II

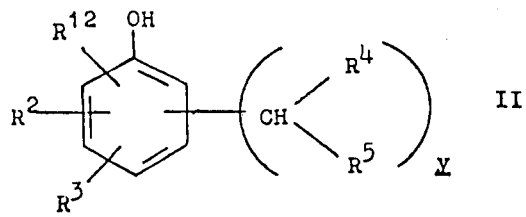

wherein
R², R³, R⁴ and R⁵ are as previously defined for formula I and R¹² is as defined for R¹;
y is the integer 1 or 2
in the presence of an acid catalyst at a temperature of from 100° to 350°C with 2 moles, per mole of said alkylphenol, of an olefine in which at least one carbon atom which carries a double bond is connected exclusively to carbon atoms, that is olefines which contain the group

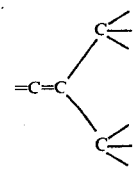

2. Process of claim 1 wherein the reaction is carried out at a temperature in the range of 110° to 250°C.
3. Process of claim 1 wherein the reaction is carried out at a temperature of from 120° to 180°C.
4. Process of claim 1 wherein the reaction is carried out at a pressure of from normal pressure to 60 atmospheres.
5. Process of claim 1 wherein the reaction is carried out at a pressure of from normal pressure up to 20 atmospheres.
6. Process of claim 1 wherein the olefine is formed in situ from isobutanol, tertiary butanol or 2-methyl-butanol-(2).
7. Process of claim 1 wherein the olefine is formed in situ from a tertiary alkyl phenol of formula II.
8. Process of claim 1 wherein the olefine is selected from the group of 2-methyl-propene, 2-methyl-butene-(1), 2-methyl-butene-(2), 2,3-dimethyl-butene-(1), 2,3-dimethyl-butene-(2), and 2-methyl-2-phenyl-propene-(1).
9. Process of claim 1 wherein said alkyl phenol is selected from the group of o-, m- and p-isopropyl-phenol; o-, m- and p-cyclopentyl-phenol; o-, m- and p-cyclohexyl-phenol; o-, m- and p-isobutyl-phenol; 1-phenyl-1-(4-hydroxy-phenyl)-ethane; 3-methyl-6-isopropyl-phenol; 3-methyl-5-isopropyl-phenol; 2-ethyl-4-cyclohexyl-phenol; 2-methyl-4-isobutyl-phenol; 2-chloro-4-isopropyl-phenol; 3,5-diisopropyl-phenol, 3,5-dicyclopentyl-phenol, 3,5-di-sec.-butyl-phenol, 3,5-dicyclohexyl-phenol, 3-isopropyl-5-cyclopentyl-phenol, 3-cyclopentyl-5-sec.-butyl-phenol, 2,6-diisopropylphenol, 2,6-dicyclopentyl-phenol, 2-isopropyl-6-cyclopentylphenol and 3,4-diisopropylphenol.
10. Process of claim 7 wherein the tertiary alkyl-phenol is tertiary butylphenol.
11. Process of claim 7 wherein the alkyl phenol of formula II and the tertiary alkyl phenol are the same.

* * * * *

UNITED STATES PATENT AND TRADEMARK OFFICE
CERTIFICATE OF CORRECTION

PATENT NO. : 3,954,889
DATED : May 4, 1976
INVENTOR(S) : Alfons Klein et al

It is certified that error appears in the above-identified patent and that said Letters Patent are hereby corrected as shown below:

[57], 2nd column, after formula and
"wherein
X is sulphur or the group" insert

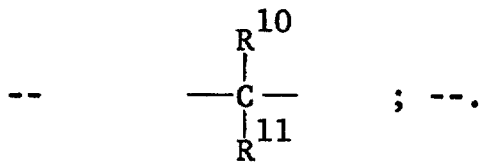

Column 4, line 22, "=0 2" should read -- =2 --.

Column 9, line 54, "indicted" should read -- indicated --.

Column 13, lines 12 et seq, delete the formula shown and substitute the formula shown at lines 30 et seq.

Column 13, lines 30 et seq, delete the formula shown and substitute the formula shown at lines 12 et seq.

Signed and Sealed this

Seventh Day of September 1976

[SEAL]

Attest:

RUTH C. MASON
Attesting Officer

C. MARSHALL DANN
Commissioner of Patents and Trademarks